Dec. 6, 1949. G. MERRILL Plant Pat. 905
PEACH TREE
Filed Sept. 24, 1948
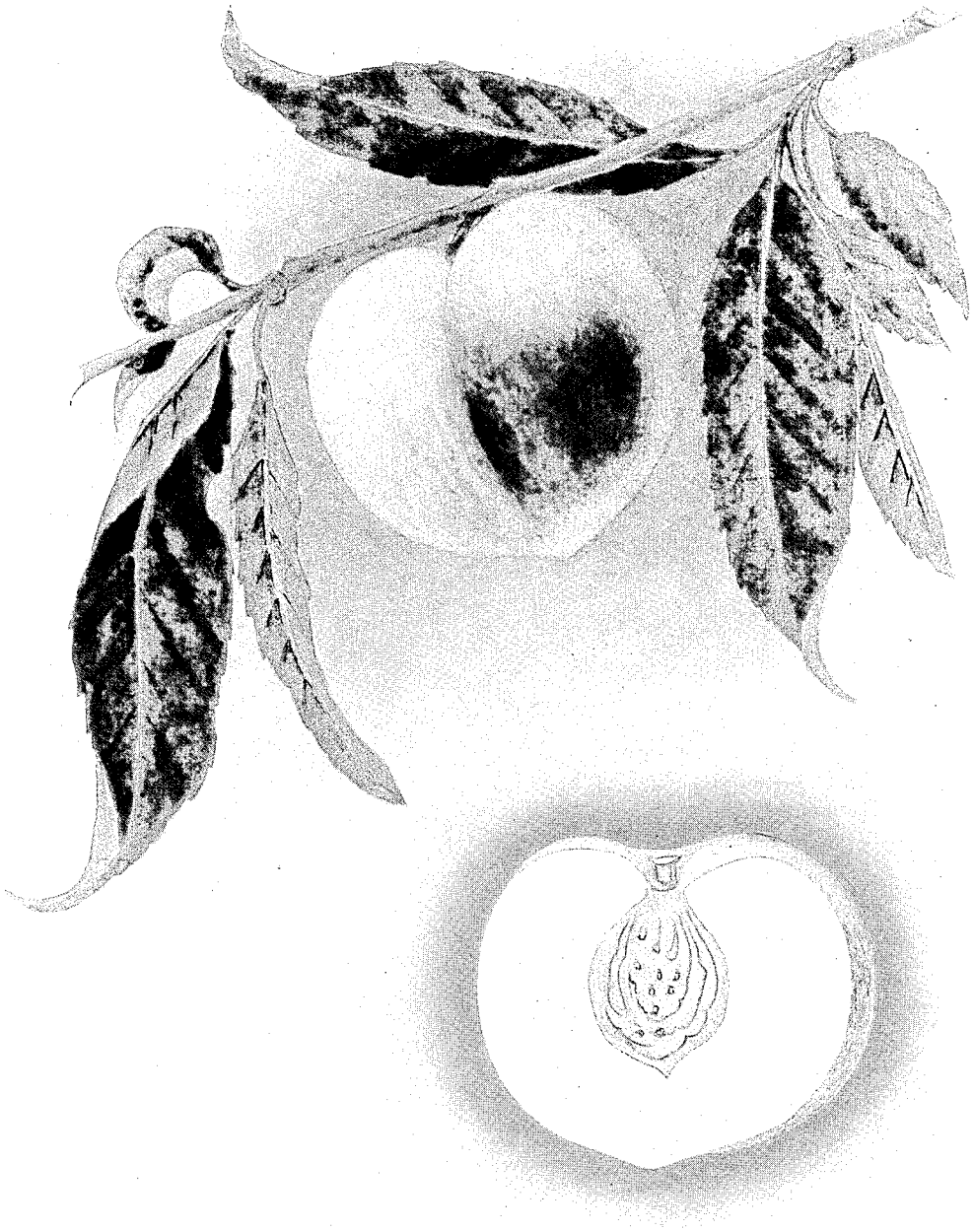
WITNESS
Addison E Avery
INVENTOR
Grant Merrill
Webster & Webster
ATTYS.

Patented Dec. 6, 1949

Plant Pat. 905

UNITED STATES PATENT OFFICE

905

PEACH TREE

Grant Merrill, Red Bluff, Calif.

Application September 24, 1948, Serial No. 50,961

1 Claim. (Cl. 47—62)

This invention relates to a new and distinct variety of peach tree which bears free stone fruit closely resembling the fruit of the J. H. Hale variety; the primary advantageous feature of the present variety being the early ripening period of its fruit, which period is approximately five weeks ahead of said J. H. Hale variety. In an average season the date of first picking is June 15th to 25th, and the date of last picking is June 25th to 30th.

Additionally, the present variety of peach tree is distinguishable from the J. H. Hale variety by reason of having pollen and being self-fertile.

Further, the present variety has a tree which is strong, vigorous, and large, as compared to the tree of the J. H. Hale variety.

While the present variety is distinguished from the J. H. Hale variety, as above, it bears fruit having certain desirable characteristics of the same, to-wit, fruit which is generally round, large, firm of flesh, and highly colored.

The present variety is a freestone peach especially useful as fresh eating or dessert peach, being adaptable to either local or distant markets; the shipping quality being good, including long distance. The fruit is also good for culinary use.

Origin of the variety was by, and on the ranch of, applicant at Red Bluff, California, as follows:

Seeds were gathered by applicant from a J. H. Hale peach tree growing next to a block of many varieties of peaches, and such seeds were planted. From the resultant seedlings one was selected as being of special merit, being identified in applicant's records as the C 1–8. It is believed that the J. H. Hale was crossed with the Arp in producing the C 1–8, as it and many of its progeny resemble the Arp. Open pollenated seeds of the C 1–8 variety were then planted, and of the resultant seedlings one was selected as a new and distinct variety, being that claimed herein, and which is identified in applicant's records as the C 7–55.

Since its origination the variety has been asexually reproduced, and the reproductions carry forward each of the mentioned novel characteristics of the parent tree C 7–55, including the early ripening period of the fruit. The first budding was in May, 1944, and the trees were planted in February, 1945, having now come into full bearing. Careful observation of such reproductions, and comparison of them with the parent tree, gives full support to the facts recited above in this paragraph.

In the original drawings:

Fig. 1 is a perspective view of the fruit of the variety as attached to a twig with leaves.

Fig. 2 is a sectional view taken axially of the fruit, with the stone exposed.

Referring now in detail to the new and distinct variety of peach tree, the following is a detailed description, in outline, of such tree and its fruit:

Tree: Medium size; medium vigorous; upright—spreading. Medium dense; vase formed. Productive; regular bearer.

Trunk: Medium slender; medium shaggy.

Branches: Medium stocky; medium shaggy. Brown.

*Lenticels.*—Few to medium in number; medium size.

Leaves:

*Length.*—5½ inches.

*Width.*—1¼ inches to 1¾ inches. Medium size. Oval lanceolate. Pointed. Medium thick; medium green. Smooth.

*Margin.*—Finely crenate.

*Petiole.*—Medium long; medium thick.

*Glands.*—Average number mostly two; opposite; small; globose; green.

*Position.*—Mostly on base of leaf blade.

*Stipules.*—On very new growth, dropping off early.

Flower buds: Medium size; short; obtuse. Free. Pubescent.

Flowers: Dates of first and full bloom—average, March 1 and 14. Medium late. Small size. Light pink.

Fruit: Maturity when described, eating ripe.

*Size.*—Uniform; large. Axial diameter—2⅝ inches to 3 inches. Transverse in suture plane—2⅝ inches to 3 inches. Transverse cheek to cheek—2⅝ inches to 3 inches.

*Form.*—Uniform; symmetrical; globose; not compressed.

*Suture.*—Shallow. Has slight depression toward pistil point.

*Ventral surface.*—Rounded. Lipped only slightly.

*Cavity.*—Rounded; abrupt. Elongated in suture plane and suture showing on one side. Depth—⅜ inch; breadth—⅜ inch; length—¾ inch. Markings—none.

*Base.*—Rounded.

*Apex.*—Short; rounded to truncate; occasionally depressed. Pistil point—apical.

Skin: Medium tough; moderately free from flesh. Tendency to crack—none. Color—gold and yellow under-color; red over-color. Striped and splashed deep red to ¾ of peach.

Flesh: Yellow. Surface of pit cavity—pale yellow.

*Amygadalin.*—Scant.
*Juice.*—Abundant; rich.
*Texture.*—Medium fine; firm melting.
*Fibres.*—Few; tender.
*Ripens.*—Evenly.
*Flavor.*—Mildly sub-acid.
*Aroma.*—Moderate.
*Eating quality.*—Best.

Stone: Free when soft ripe. Parts from flesh smoothly when soft.

*Size.* — Medium. Length — 1⅜ inches; breadth—⅞ inch; thickness—⅝ inch.
*Form.*—Oval to obovate.
*Base.*—Slightly oblique.
*Hilum.*—Oval.
*Apex.*—Acute to acuminate.
*Sides.*—Equal.
*Surface.*—Slightly furrowed toward base; pitted and grooved from base throughout.
*Pits.*—Circular to elongated.
*Ventral edge.*—Very thick; slight wing.
*Dorsal edge.*—Narrow with deep groove throughout.
*Ridges.*—On either side interrupted or continuous.
*Color of stone.*—Light tan.
*Tendency to split.*—Very slight.

The keeping quality of the fruit is medium; and the resistance of the variety to insects is good and to disease is medium. Shipping quality is good, local or distant.

The fruit of the present variety more nearly resembles the J. H. Hale variety than any other, retaining its desirable large size, generally round shape, firm flesh, and high exterior color; being gold and yellow with a red over-color, striped and splashed over approximately three-fourths of its outside area. The average five-weeks earlier ripening period is an extreme advantage in the trade and, as hereinbefore described, is the primary distinguishing feature between said varieties; each bearing fruit especially adapted for fresh eating or dessert use, and also for culinary purposes.

The tree and its fruit as herein described may vary in slight detail due to climatic and soil conditions under which the variety may be grown.

Having thus described my invention, I claim:

A new and distinct variety of peach tree characterized by fruit bearing close similarity to the fruit of the J. H. Hale variety but having a ripening period which is approximately five weeks earlier; the variety having pollen, being self-fertile, and the tree being strong, vigorous, and large.

GRANT MERRILL.

No references cited.